(12) United States Patent
Zhang et al.

(10) Patent No.: US 8,227,247 B2
(45) Date of Patent: Jul. 24, 2012

(54) METHOD OF GENERATING MYELINATING OLIGODENDROCYTES

(75) Inventors: Su-Chun Zhang, Middleton, WI (US);
Baoyang Hu, Madison, WI (US);
Zhong-Wei Du, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 563 days.

(21) Appl. No.: 12/338,749

(22) Filed: Dec. 18, 2008

(65) Prior Publication Data

US 2010/0159595 A1 Jun. 24, 2010

Related U.S. Application Data

(60) Provisional application No. 61/015,407, filed on Dec. 20, 2007.

(51) Int. Cl.
*C12N 5/00* (2006.01)
*C12N 5/02* (2006.01)
*A01N 63/00* (2006.01)
*A01N 65/00* (2009.01)

(52) U.S. Cl. ........................................ 435/377; 435/368

(58) Field of Classification Search ........................ None
See application file for complete search history.

(56) References Cited

U.S. PATENT DOCUMENTS

| | | | |
|---|---|---|---|
| 6,887,706 B2 | 5/2005 | Zhang et al. | |
| 7,285,415 B2 | 10/2007 | Keirstead et al. | |
| 2005/0095706 A1 * | 5/2005 | Zhang et al. | 435/368 |
| 2005/0101014 A1 | 5/2005 | Keirstead et al. | |
| 2008/0227137 A1 * | 9/2008 | Zhang et al. | 435/29 |

FOREIGN PATENT DOCUMENTS

WO 2004007696 A2 1/2004

OTHER PUBLICATIONS

Hu et al., Nat Protoc. 4(11): 1614-1622, 2009.*
Hu et al., Development 136:1443-1452, 2009.*
Faulkner J. & Keirstead H., "Human embryonic stem cell-derived oligodendrocyte progenitors for the treatment of spinal cord injury," Transpl. Ummunol. 15:131-142 (2005).
Keirstead H. et al., "Human embryonic stem cell-derived oligodendrocyte progenitor cell transplants remyelinate and restore locomotion after spinal cord injury," J. Neurosci. 25:4694-4705 (2005).
Nistor G. et al., "Human embryonic stem cells differentiate into oligodendrocytes in high purity and myelinate after spinal cord transplantation," Glia 49:385-396 (2005).
Cloutier F. et al., "Transplantation of human embryonic stem cell-derived oligodendrocyte progenitors into rat spinal cord injuries does not cause harm," Regen. Med. 1:469-479 (2006).
Zhang S. et al., "In vitro differentiation of transplantable neural precursors from human embryonic stem cells," Nat. Biotechnol. 19:1129-1133 (2001).
Li X. et al., "Specification of motoneurons from human embryonic stem cells," Nat. Biotechnol. 23:215-221 (2005).
Sinha S. & Chen J., "Purmorphamine activates the Hedgehog pathway by targeting Smoothened," Nature Chem. Biol. 2:29-30 (2006).
Du Z. et al., "Induced expression of Olig2 is sufficient for oligodendrocyte specification but not for motoneuron specification and astrocyte repression," Mol. Cellular Neurosci. 33:371-380 (2006).
Shin S., et al., "Stage-Dependent Olig2 Expression in Motor Neurons and Oligodendrocytes Differentiated from Embryonic Stem Cells," Stem Cells and Development 16:131-141 (2007).
Frank-Kamenetsky M. et al., "Small-molecule modulators of Hedgehog signaling: identification and characterization of Smoothened agonist and antagonist," Journal of Biology vol. 1, Issue 2, Article 10, 2006.

* cited by examiner

*Primary Examiner* — Daniel E Kolker
*Assistant Examiner* — Stacey MacFarlane
(74) *Attorney, Agent, or Firm* — Quarles & Brady, LLP

(57) ABSTRACT

A method of differentiating embryonic stem cells into oligodendroglial precursor cells and oligodendroglial cells by culturing a population of cells comprising a majority of cells that are characterized by a neural tube-like rosette morphology and are Pax6+/Sox1+ into a population of cells that are PDGFRα+.

16 Claims, 13 Drawing Sheets

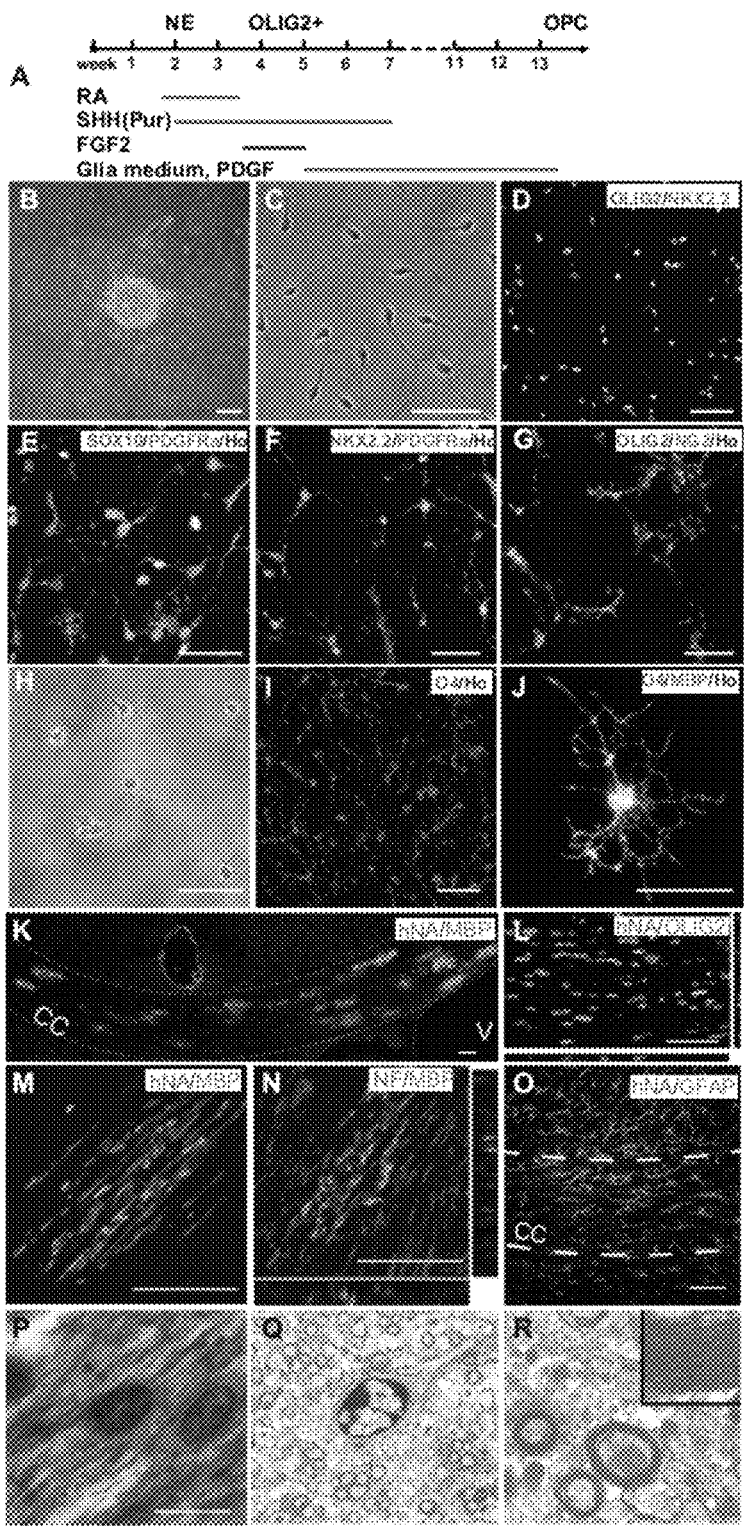

METHOD OF GENERATING MYELINATING OLIGODENDROCYTES

CROSS-REFERENCE TO RELATED APPLICATION

This application claims the benefit of U.S. Patent Application No. 61/015,407, filed on Dec. 20, 2007, which is incorporated herein by reference in its entirety.

STATEMENT REGARDING FEDERALLY SPONSORED RESEARCH OR DEVELOPMENT

This invention was made with United States government support awarded by the following agency: NIH NS045926. The United States government has certain rights in this invention.

BACKGROUND

Oligodendrocytes, the myelinating glia in the central nervous system (CNS), are differentiated chiefly from neuroepithelial cells of the ventral neural tube. In ventral neural tube-derived neuroepithelial cells, a helix-loop-helix transcription factor, Olig2, is activated in response to ventrally derived sonic hedgehog (SHH). Alberta J, et al., "Sonic hedgehog is required during an early phase of oligodendrocyte development in mammalian brain," Mol. Cell. Neurosci. 18:434-41 (2001); Fu H, et al., "Dual origin of spinal oligodendrocyte progenitors and evidence for the cooperative role of Olig2 and Nkx2.2 in the control of oligodendrocyte differentiation," Development 129:681-693 (2002); Ligon K, et al., "Olig gene function in CNS development and disease," Glia 54:1-10 (2006); Lu Q, et al., "Sonic hedgehog-regulated oligodendrocyte lineage genes encoding bHLH proteins in the mammalian central nervous system," Neuron 25:317-329 (2000); Rowitch D, et al., "Sonic hedgehog regulates proliferation and inhibits differentiation of CNS precursor cells," J. Neurosci. 19:8954-8965 (1999); Zhou Q, et al., "The bHLH transcription factor Olig2 promotes oligodendrocyte differentiation in collaboration with Nkx2.2," Neuron 31:791-807 (2001); and Zhou Q, et al., "Identification of a novel family of oligodendrocyte lineage-specific basic helix-loop-helix transcription factors," Neuron 25:331-343 (2000). Interestingly, Olig2 is expressed in a restricted domain of the spinal cord ventricular zone that sequentially gives rise to motor neurons and then oligodendrocytes (i.e., sequential model). That is, Olig2-expressing neuroepithelial cells in the spinal cord give rise to motor neurons during a neurogenic phase. Thereafter, these Olig2-expressing progenitors down-regulate neurogenic phase. Thereafter, these Olig2-expressing progenitors down-regulate neurogenic transcription factors such as Ngn2 and Pax6, and begin to express Nkx2.2, an oligodendroglial transcription factor. Fu et al., supra; and Qi Y, et al., "Control of oligodendrocyte differentiation by the Nkx2.2 homeodomain transcription factor," Development 128:2723-2733 (2001). Thus, this dual function of Olig2 is controlled by spatio-temporal changes in the domains of expression of several other transcription factors in relation to Olig2.

In addition to ventrally derived oligodendrocyte precursor cells (OPCs), a smaller population of OPCs are generated from the dorsal neural tube. Battiste J, et al., "Ascl1 defines sequentially generated lineage restricted neuronal and oligodendrocyte precursor cells in the spinal cord," Development 134:285-293 (2007); Cai J, et al., "Generation of oligodendrocyte precursor cells from mouse dorsal spinal cord independent of Nkx6 regulation and SHH signaling," Neuron 45:41-53 (2005); Fogarty M, et al., "A subset of oligodendrocytes generated from radial glia in the dorsal spinal cord," Development 132:1951-1959 (2005); and Vallstedt A, et al., "Multiple dorsoventral origins of oligodendrocyte generation in the spinal cord and hindbrain," Neuron 45:55-67 (2005). While dorsally derived neuroepitheilial cells appear SHH-independent, they nevertheless must express Olig2 to become OPCs. Cai et al., supra.

Although one would predict that human OPCs could be obtained via methods akin to those used in other species, such as mice, independent laboratories have been consistently unsuccessful in generating OPCs from expanded human neural stem/progenitor cells using those methods. Chandran S, et al., "Differential generation of oligodendrocytes from human and rodent embryonic spinal cord neural precursors," Glia 47:314-324 (2004); Roy N, et al., "Identification, isolation, and promoter-defined separation of mitotic oligodendrocyte progenitor cells from the adult human subcortical white matter," J. Neurosci. 19:9986-9995 (1999); Windrem M, et al., "Fetal and adult human oligodendrocyte progenitor cell isolates myelinate the congenitally dysmyelinated brain," Nat. Med. 10:93-97 (2004); and Zhang S, et al., "Tracing human oligodendroglial development in vitro," J. Neurosci. Res. 59:421-429 (2000). Human embryonic stem cells (hESCs) have been reported to differentiate to OPCs after expansion of hESC-derived neural progenitors in the presence of either FGF2 or EGF or both. Izrael M, et al., "Human oligodendrocytes derived from embryonic stem cells: effect of noggin on phenotypic differentiation in vitro and on myelination in vivo," Mol. Cell. Neurosci. 34:310-323 (2007); Kang S, et al., "Efficient induction of oligodendrocytes from human embryonic stem cells," Stem Cells 25:419-424 (2007); Nistor G, et al., "Human embryonic stem cells differentiate into oligodendrocytes in high purity and myelinate after spinal cord transplantation," Glia 49:385-396 (2005). It is unknown, however, whether the growth factors specify OPCs by deregulating the dorsal-ventral patterning as in mice or simply expand spontaneously differentiated OPCs.

As in other vertebrates, human OPCs express Olig2. Jakovcevski I and Zecevic N, "Olig transcription factors are expressed in oligodendrocyte and neuronal cells in human fetal CNS," J. Neurosci. 25:10064-10073 (2005). However, whether Olig2 transcription is necessary and how neural progenitors transform to OPCs in humans remain uninvestigated. Answers to the above questions are instrumental to an understanding of the biology of human neural development, as well as to an ability to promote remyelination in humans. As such, additional methods of generating oligodendrocytes from human embryonic stem cells (hESCs) are needed in the art.

BRIEF SUMMARY OF THE INVENTION

Specification of distinct cell types from pluripotent stem cells is key to a potential application of these naïve pluripotent cells in regenerative medicine. Here, we demonstrate that transcription of Olig2 is required for OPC specification from hESCs. Consistent with findings in mouse OPC development, specification of OPCs from hESC-derived neureopithelial cells depends on SHH-induced Olig2 expression at multiple stages. In contrast to findings with mouse OPC development, FGF2 exposure blocked human OPC specification from neuroepithelial cells when continuously applied to Olig2+ progenitor cells. Moreover, human OPC specification followed a timing inherent to human development and in particular, transformation from gliogenic human Olig2+ progenitors to OPCs was prolonged when compared to other species and was not altered by factors such as SHH, Noggin, EGF and FGF2.

In a first aspect, the present invention is a method of generating a population of OPCs comprising a synchronous population of cells that express Nkx2.2, Sox10, Olig2 and PDGFRα and are cultured from pluripotent stem cells, such as ESCs and iPS cells. In one embodiment, the method includes propagating ESCs or iPS cells into a synchronous population of neural stem cells in the form of neural tube-like rosettes (Pax6+/Sox1+). The method also includes culturing the neural tube-like rosettes in a neural induction medium containing retinoic acid (RA) and an activator of a SHH pathway into an Olig2-expressing cell population. Optionally, the medium contains FGF-2 to inhibit motor neuron generation. The method also includes culturing the Olig2-expressing cell population in a glial differentiation medium containing the activator of the SHH pathway into OPCs.

By "OPCs," we mean cells that exhibit a bipolar morphology and express Nkx2.2, NG2, Olig2, Sox10 and PDGFRα and can differentiate into myelin-producing oligodendrocytes. We use the term "oligodendroglial" interchangeably with oligodendrocyte.

The total time period between the propagation of ESCs to development of early rosettes is typically between 8-10 days. Preferably, the total population of Pax6+/Sox1− cells is at least 80%, preferably 90% of the total cell population. The total time period between the propagation of neural tube-like rosettes into Olig2+/PDGFRa+ cells is up to about eight weeks. Preferably, the total population of OPCs is at least 80%, preferably 90% of the total cell population.

In a second aspect, the present invention is a method of generating a population of oligodendrocytes comprising a synchronous population of cells cultured from ESCs that express Nkx2.2, Olig2, Sox10 and PDGFRα. In one embodiment, the method includes propagating pluripotent stem cells into a synchronous population of neural stem cells in the form of neural tube-like rosettes (Pax6+/Sox1+). The method also includes culturing the neural tube-like rosettes in a neural induction medium containing retinoic acid (RA) and an activator of a SHH pathway into an Olig2-expressing cell population. Optionally, the medium contains FGF-2, The method also includes culturing the Olig2-expressing cell population in a glial differentiation medium containing the activator of the SHH pathway into OPCs. The method also includes culturing the OPCs in the glial differentiation medium on substrate containing basement membrane protein (ie, laminin), but in the absence of the activator of the SHH pathway into oligodendrocytes.

By "oligodendrocytes," we mean both immature cells that express O4 and mature cells expressing GC(O1), myelin basic protein (MBP), Sox10 and proteolipid protein (PLP) that can differentiate in vivo into myelin-producing oligodendrocytes.

In some embodiments of either aspect, the ESCs or iPS cells are differentiated into the neural tube-like rosettes through an early rosette (Pax6+/Sox1−) intermediate. In some embodiments of either aspect, the activator of the SHH pathway is SHH or purmorphamine.

In a third aspect, the invention is a population of cells created by the methods disclosed herein.

In a fourth aspect, the present invention is a method of testing the cell populations described above to screen agents for the ability to affect normal human neural development.

Other objects, advantages and features of the present invention will become apparent after review of the specification, claims and drawings.

BRIEF DESCRIPTION OF THE DRAWINGS

FIGS. 6A-6R: Maturation and myelination of hESC-derived OPCs. (A) Summarized procedures for directed differentiation of OPCs from hESCs. (B) Bipolar cells are present surrounding the progenitor cluster 3 days following plating. (C) Dissociated OPCs exhibit a bipolar morphology. The OPCs co-express OLIG2/NKX2.2 (D), SOX10/PDGFRα (E), NKX2.2/PDGFRα (F), and OLIG2/NG2 (G). (H, I) Six weeks following OPC differentiation, cells exhibit multipolar and web-like processes, and express O4. (J) In an additional month, some cells express MBP. (K) Three months following transplantation, the grafted cells, revealed by hNA and MBP, preferentially localize in the corpus callosum (CC, outlined area). (L) All of the human cells are positive for OLIG2. (M) The human cells exhibit multiple MBP+ processes. (N) Confocal analysis shows adjacent expression of MBP+ human cell fibers with NF+ axons in the corpus callosum. (O) The hNA+ cells are negative for GFAP. (P) Toluidine blue staining shows large amount of myelin sheaths in the transplanted brain. (Q) EM shows a typical oligogodendrocyte surrounded by many myelin profiles in the grafted brain. (R) Higher magnification shows compact myelin sheaths in the grafted brain with identifiable major dense lines (inset). Bar=50 μm in B-I, O-P and 10 μm in J. Magnification is 6 k for G, 20 k and 60 k for H and inset, respectively.

DESCRIPTION OF PREFERRED EMBODIMENTS

Figure 1:
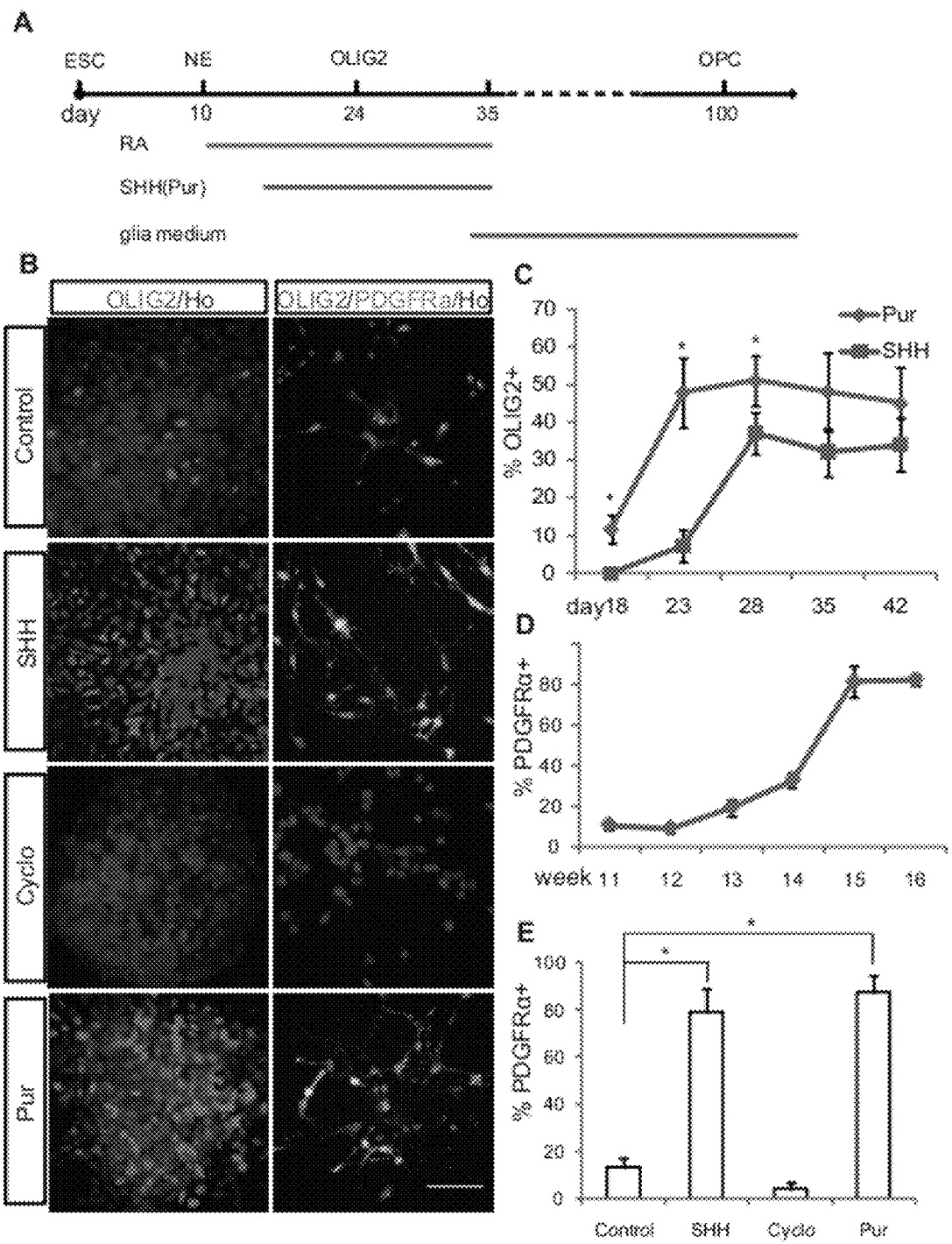
FIGS. 1A-1E: SHH-dependent OLIG2 expression for hESC differentiation to OPCs. (A) Experimental paradigm showing differentiation of OLIG2 progenitors and OPC differentiation in the glial medium. (B) OLIG2-expressing progenitors and OLIG2/PDGFRα double positive OPCs are present in the control, SHH, and purmorphamine (Pur)-treated cultures but rarely in the cyclopamine-treated cultures at day 35 and day 100, respectively. (C) Time course of OLIG2 expression in response to Pur (1 μM) and SHH (100 ng/ml). (*p=0.011, 0.008 and 0.014 at day 18, 23 and 28, respectively). (D) PDGFRα$^+$ OPCs first appear after 10 weeks of differentiation and reach the plateau at the 15th week. (E) Comparative effect of SHH, purmorphamine (Pur), and cyclopamine (cyclo) on the efficiency of OPC differentiation at the 15$^{th}$ week. % PDGFRα in (D) and (E) stands for the proportion of PDGFRα$^+$ cells among total cells. Bar=50 μm. Ho: Hoechst 33258 stained nuclei.

Applicants herein disclose a method for generating oligodendrocytes, preferably from pluripotent cells such as from hESCs or iPS cells. The preferred methods are generally described in Table 1 below and in more detail in Table 2 below.

Specifically, Applicants disclose a method of differentiating early rosettes (Pax6+/Sox1−) from pluripotent stem cells, such as ESCs or iPS cells, through an embryoid body (EB) intermediate. (One may also create the Pox6+/Sox1− cells from multipotent cells, such as fetal neural stem cells.) By differential treatment, Applicants differentiated these early rosettes into neural tube-like rosettes (Pax6+/Sox1+) that were then suitable for development into OPCs.

TABLE 1

General scheme for generating OPCs. (All time designations are ±10%.)
Generation of Oligodendrocyte Precursor Cells from hESCs

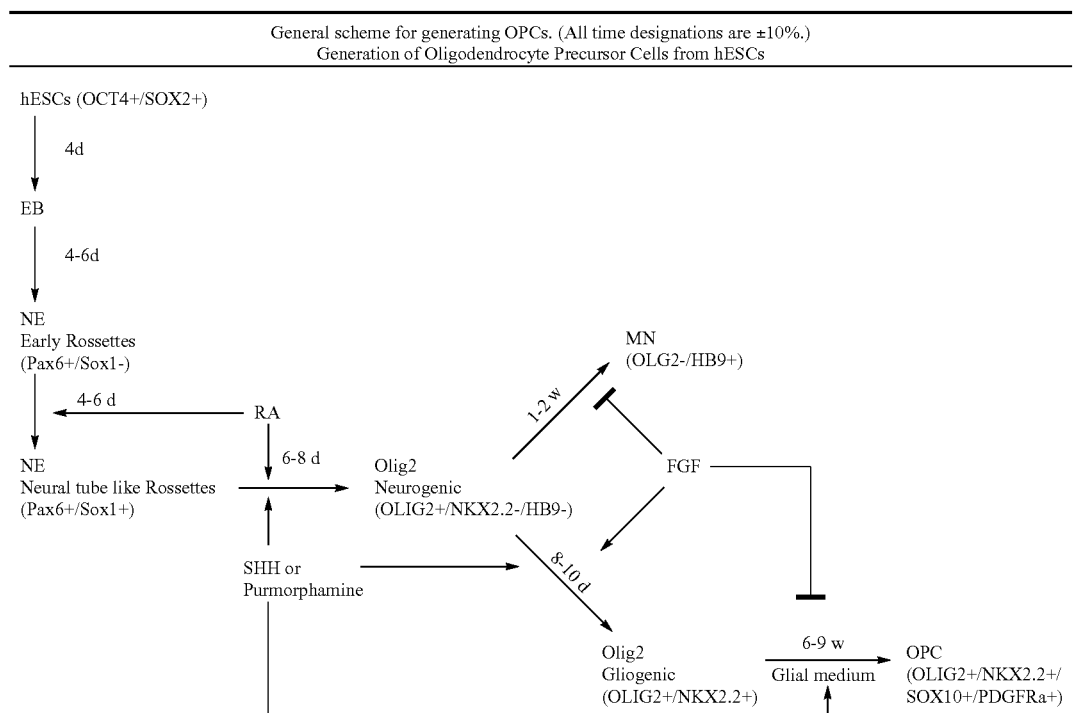

| TERM | DEFINITION | TERM | DEFINITION |
|---|---|---|---|
| HESCs | human embryonic stem cells | EB | embryoid bodies |
| NE | neuroepithelial cells | RA | retinoic acid |
| SHH | sonic hedgehog | Olig2 | oligodendrocyte lineage transcription factor 2 positive cells |
| FGF | Fibroblast Growth Factor | MN | Motor Neuron cells |
| OPC | Oligodendrocyte Precursor Cells | neurogenic | with the potencies for both neurons and glia |
| gliogenic | with potency to glia, oligodendrocyte in this case | glia medium | modified from Bottenstein-Sato medium (DMEM with insulin); B27; N1 supplement, 60 ng/ml T3, 100 ng/ml biotin, 1 μM cAMP; see Bottenstein J, et al., "The growth of cells in serum-free hormone-supplemented media," Methods Enzymol. 58: 94-109 (1979). |

TABLE 1-continued

Motor neuron markers
   HB9 HLXB9 protein, MNX1 protein, homeo box HB9 protein [1, 2]
OPCs markers
   OLIG2 [3]
   NKX2.2 NK2 transcription factor related, locus 2 [4, 5]
   PDGF-AA platelet-derived growth factor AA, homodimer of A chain of platelet-derived growth factor [6, 7]
   NG2 chondroitin sulfate proteoglycan 4 [8]
   SOX10 SRY (sex determining region Y)-box 10 protein [9, 10]
immature oligodendrocyte markers
   O4 O4 antigen, ganglioside expressed on immature oligodendrocytes [11, 12]
mature oligodendrocyte markers
   MBP myelin basic protein [13]
   CNP 2',3'-Cyclic-Nucleotide Phosphodiesterases [14]
Reference list 1. Novitch, B. G., Chen, A. I. & Jessell, T. M. Coordinate Regulation of Motor Neuron Subtype Identity and Pan-Neuronal Properties by the bHLH Repressor Olig2. Neuron 31, 773-789(2001).
2. Arber, S. et al. Requirement for the Homeobox Gene Hb9 in the Consolidation of Motor Neuron Identity. NEURON-CAMBRIDGE MA- 23, 659-674(1999).
3. Zhou, Q. & Anderson, D. J. The bHLH Transcription Factors OLIG2 and OLIG1 Couple Neuronal and Glial Subtype Specification. Cell 109, 61-73(2002).
4. Zhou, Q., Choi, G. & Anderson, D. J. The bHLH Transcription Factor Olig2 Promotes Oligodendrocyte Differentiation in Collaboration with Nkx2.2. Neuron 31, 791-807(2001).
5. Qi, Y. et al. Control of oligodendrocyte differentiation by the Nkx2.2 homeodomain transcription factor. Development 128, 2723-2733(2001).
6. Hall, A., Giese, N. & Richardson, W. Spinal cord oligodendrocytes develop from ventrally derived progenitor cells that express PDGF alpha-receptors. Development 122, 4085-4094(1996).
7. Ellison, J. A. & de Vellis, J. Platelet-derived growth factor receptor is expressed by cells in the early oligodendrocyte lineage. J Neurosci Res 37, 116-28(1994).
8. Stallcup, W. & Beasley, L. Bipotential glial precursor cells of the optic nerve express the NG2 proteoglycan. J. Neurosci. 7, 2737-2744(1987).
9. Kuhlbrodt, K. et al. Sox10, a Novel Transcriptional Modulator in Glial Cells. J. Neurosci. 18, 237-250(1998).
10. Terminal differentiation of myelin-forming oligodendrocytes depends on the transcription factor Sox10. (2002).at <http://genesdev.cshlp.org/content/16/2/165.abstract>
11. Bansal, R. et al. Multiple and novel specificities of monoclonal antibodies O1, O4, and R-mAb used in the analysis of oligodendrocyte development. J Neurosci Res 24, 548-57(1989).
12. Sommer, I. & Schachner, M. Monoclonal antibodies (O1 to O4) to oligodendrocyte cell surfaces: an immunocytological study in the central nervous system. Dev Biol 83, 311-27(1981).
13. Givogri, M. I. et al. Expression and regulation of golli products of myelin basic protein gene during in vitro development of oligodendrocytes. J Neurosci Res 66, 679-90(2001).
14. Kim, S. U., McMorris, F. A. & Sprinkle, T. J. Immunofluorescence demonstration of 2':3'-cyclic-nucleotide 3'-phosphodiesterase in cultured oligodendrocytes of mouse, rat, calf and human. Brain Res 300, 195-9(1984).

Differentiation of Neuroepithelial Cells (Neural Stem Cells) from hESCs or iPS Cells.

In the Example below hESCs were derived from a 5.5 day-old human embryo. (See Thomson J, et al., "Embryonic stem cell lines derived from human blastocysts," Science 282:1145-1147 (1998), incorporated herein by reference as if set forth in its entirety.) Alternatively, the method may begin with other pluripotent stem cells, such as iPS cells (see U.S. publication 2008/0233610 published Sep. 25, 2008, incorporated by reference herein as if set forth in its entirety.)

As shown in the Examples, generation of neuroepithelial cells will involve formation of EBs in a suspension culture for 4-6 days, followed by adherent culture in the presence of growth factors, preferably FGF2 or FGF8, for 4-5 days when cells in the center of each colony will become columnar and will organize into a rosette form. [See Zhang S, et al., "In vitro differentiation of transplantable neural precursors from human embryonic stem cells," Nat. Biotechnol. 19:1129-1133 (2001), incorporated herein by reference as if set forth in its entirety.] FGF4 and FGF9 are also suitable growth factors.

Columnar cells in the rosettes will express a neural transcription factor, Pax6, but will not express another neural transcription factor, Sox1. We call these rosettes "early rosettes" because they appear early and form a monolayer of columnar cells without a lumen. Typically, every single colony will possess early rosettes. The total population of early rosette cells is typically at least 70% of the total cells.

Further culture of these early rosettes for 4-6 days will lead to formation of neural tube-like rosettes. The neural tube-like rosettes are formed by multiple layers of columnar cells with a clear lumen. The cells in these rosettes express Sox1 in addition to Pax6. Progression from early rosettes to neural tube-like rosettes is in about 4-6 days under serum-free culture conditions in the presence of FGF2, FGF4, FGF8 or FGF9 at 10-20 ng/ml, but preferably in the presence of RA at 0.001-1 µM, preferably between 0.05-0.3 µM and most preferably between 0.1-0.15 µM, all ±10%. The process of neuroepithelial differentiation, from ESCs to formation of neural tube-like rosettes, will be complete in 14-16 days.

Development of neuroepithelial cells from hESCs in this culture system compared well to the 19-21 days that such development takes in a human embryo. In normal human development, neural tube forms at 20-21 days. Thus, neuroepithelial differentiation from hESCs mirrored normal human embryo development. (See Zhang S, "Embryonic stem cells for neural replacement therapy: prospects and challenges," J. Hematother. Stem Cell Res. 12:625-634 2003).

The two-stage neuroepithelial development, as evidenced by morphological transformation and clear-cut gene expression patterns, has been described previously. See Zhang et al. (2001), supra. Interestingly, Pax6 and Sox1 were expressed at the same time by neuroepithelial cells when neural tube forms in frogs, zebrafish, chicks and mice. Pevny L, et al., "A role for SOX1 in neural determination," Development 125:1967-1978 (1998). As such, sequential Pax6 and Sox1 expression along neuroepithelial differentiation in hESCs is unique to humans.

Pax6+/Sox1− neuroepithelial cells represent the earliest neuroepithelial cells thus far identified. The functional significance of these cells is relevant to this disclosure in that the Pax6+/Sox1− neuroepithelial cells in the early rosettes were efficiently induced to neural tube-like rosettes, which eventually become OPCs (Table 1, see above).

In our Examples, every differentiating ESC colony formed neural tube-like rosettes. The neuroepithelial cells represented at least 70-90% of the total differentiated cells. The neural tube-like rosettes were purified through treatment with a low concentration of dispase and differential adhesion (described in U.S. Pat. No. 6,887,706).

As shown in Table 1, one would also treat the NE cells with SHH or its agonist at concentrations defined below.

Differentiation of OPCs from Neuroepithelial Cells (Neural Stem Cells).

The final step of the present invention is the differentiation of OPCs from neural epithelial cells. As shown in Table 1, this will involve incubation of the steps of the cells with both retinoic acid and an agent that activates a sonic hedgehog pathway to form Olig2 expressing cells. These cells are then further incubated with an agent that activates a sonic hedgehog pathway and FGF to form Olig2 gliogenic cells (Olig2+/NKX2.2+). Further 6-9 weeks of culture in glial medium results in OPC (Olig2+/NKX2.2+/SOX10+/PDGFRα+) cells.

In the Examples below, using hESCs in a chemically defined system, we demonstrated that activation of Olig2 by sonic hedgehog (SHH) or its agonist, purmorphamine, was required for OPC specification. Inhibition of SHH signaling by cyclopamine blocked Olig2 transcription, resulting in a lack of OPCs.

In the method of the present invention, following differentiation of Olig2-expressing progenitor cells, SHH or purmorphamine (SHH at between 50 to 500 ng/ml±10% and purmorphamine at 0.5 to 2 µM, ±10%) is needed to maintain Olig2 expression and to induce Nkx2.2 transcription in neural progenitors until post-neurogenesis in order to generate OPCs. Because of the sequential development of motor neurons and oligodendrocytes in progenitors, we found that removal of SHH or purmorphamine immediately after the phase in which motor neurons occur resulted in a loss of Olig2/Nkx2.2-expressing progenitors with subsequent lack of OPCs. Although a large number of Olig2/Nkx2.2 progenitors were present at 5 weeks of culture, OPCs expressing PDGFRα and NG2 did not appear for another 5 weeks.

FGF2, together with PDGFAA, has been shown to promote OPC differentiation/proliferation from mouse, but not human neural stem/progenitors. Addition of FGF2 following the generation of Olig2 progenitors will efficiently block the differentiation of HB9+ motor neurons and maintained Olig2 progenitors. However, continued presence of FGF2 will inhibit the expression of Olig2 and Nkx2.2, thus diminishing the production of OPCs. These findings indicate that activation of Olig2 in neural progenitors is a prerequisite step and that SHH signaling is essential in inducing and maintaining Olig2 transcription in order to specify OPCs from hESCs.

We also revealed an unusually long delay for human Olig2/Nkx2.2 progenitors to become OPCs as compared to other species. Further in vitro and in vivo analyses indicated that hESC-differentiated OPCs matured and produced myelin sheaths surrounding unmyelinated axons, suggesting potential use of these cells in myelin repair.

One may also use the methods of the present invention to create OPCs from NE cells that have not been obtained from pluripotent stem cells. For example, one may begin the method with a multipotent cell, such as fetal neural stem cells. One would create NE cells and follow the method steps to obtain OPC cells.

One may wish to obtain mature oligodendrocytes. Further culture of OPCs with half of amount of PDGF-AA, NT3 and IGF in glia medium on the substrate for another 4 weeks will result in immature oligodendrocytes. Mature oligodendrocytes expressing MBP and CNPase can be shown in vitro by co-culturing immature oligodendrocytes with mature neurons and in vivo by transplanting OPCs or immature oligodendrocytes to brains of dysmyelinated MBP mutated shiverer mice.

Cell Populations of the Present Invention.

The present invention is also a cell population created by the methods above. Specifically, in one embodiment this present invention is a population of cells created by a method of generating a population of oligodendroglial precursor cells, the method comprising the steps of differentiating isolated pluripotent stem cells into a population of cells having a neural tube-like rosette morphology that are Pax6+/Sox1+, culturing neural tube-like rosette cells in the presence of retinoic acid and an agent that activates a sonic hedgehog pathway to obtain Olig2-expressing progenitor cells and culturing the Olig2-expressing progenitors cells in the presence of the agent that activates the sonic hedgehog pathway, but in the absence of retinoic acid to obtain PDGFRα+/SOX10+/OLIG2+/NKX2.2+ oligodendroglial precursor cells.

In another embodiment, the present invention is a cell population created by a method of generating a population of oligodendroglial cells, the method comprising the steps of obtaining cells having a neural tube-like rosette morphology that are Pax6+/Sox1+, culturing the neural tube-like rosette cells in the presence of retinoic acid and an agent that activates a sonic hedgehog pathway to obtain Olig2-expressing progenitor cells, culturing the progenitor cells in the presence of an agent that activates a sonic hedgehog pathway to obtain Olig2/Nkx2.2-expressing glial progenitor cells, culturing the Olig2/Nkx2.2-expressing glial progenitors in the presence of the agent that activates the sonic hedgehog pathway, but in the absence of retinoic acid, to obtain PDGFRα+ oligodendroglial precursor cells and culturing the PDGFRα+ oligodendroglial precursor cells on an extracellular matrix material in the absence of the agent that activates the sonic hedgehog pathway to obtain oligodendroglial cells.

Preferably, the populations of the present invention are at least 90% pure.

EXAMPLES

We developed a stepwise, chemically defined differentiation protocol for oligodendrocyte differentiation from hESCs that fits the process of oligodendrocyte development in a human embryo. hESCs were first differentiated to uniform neuroepithelial cells that organized into neural tube-like rosettes for two weeks (see U.S. Pat. No. 6,887,706; see also Zhang et al. (2001), supra; each of which is incorporated herein by reference as if set forth in its entirety), followed by specification of these neuroepithelial cells to Olig2-expressing motor neuron/oligodendrocyte precursor cells (Olig2 progenitor cells) in the presence of SHH over two weeks.

In some experiments, the Olig2 progenitors cells were then treated with a FGF, such as FGF2, to block motor neuron differentiation, and were maintained as Olig2 progenitors in the presence of SHH for one week. These Olig2 progenitors no longer produced motor neurons, but instead generated OPCs after eight additional weeks of SHH treatment. Therefore, the differentiation of OPCs was strictly dependent upon SHH.

We further discovered that SHH could be completely replaced by a small molecule, purmorphamine, which activates the SHH pathway for motor neuron and OPC differentiation. Using this chemically defined protocol, at least 80% of the hESC differentiated progenies were OPCs. These OPCs can become mature oligodendrocytes in the culture and produce myelin sheaths following transplantation to the brain of shiverer mice, which do not produce myelin due to mutation in the myelin basic protein (MBP) gene.

Example 1

Generation of OPCs

Methods hESCs (line H1 and H9; WiCell Research Institute; Madison, Wis.) were cultured on irradiated mouse embryonic fibroblasts (MEF) in a 6-well plate. Thomson et al., supra. hESC growth medium consisted of DMEM/F12, 15% knockout serum replacement, 1× non-essential amino acids, sodium pyruvate (1 mM), sodium bicarbonate (0.075%), I-glutamine (292 mg/ml), 2-mercaptoethanol (0.1 mM) (all reagents from Gibco; Rockville, Md.). Differentiated colonies were marked and removed physically with a pipette tip and the stem cell state was periodically monitored by expression of Oct4 and SSEA4. Pankratz M, et al., "Directed neural differentiation of human embryonic stem cells via an obligated primitive anterior stage," Stem Cells 25:1511-1520 (2007); and Thomson et al., supra.

hESCs were then differentiated to primitive neuroepithelial cells in an adherent colony culture for 10 days in a neural induction medium consisting of DMEM/F12, N2 supplement and non-essential amino acids, as detailed elsewhere. Pankratz et al., supra; and Zhang et al. (2001), supra. To pattern the primitive neuroepithelial cells to ventral spinal progenitors, differentiation cultures at day 10 were treated with RA (Sigma; St. Louis, Mo.; 100 nM) and SHH (R&D System; Minneapolis, Minn.; 100 ng/ml) (Li X, et al., "Specification of motoneurons from human embryonic stem cells," Nat. Biotechnol. 23:215-221 (2005) or with RA and purmorphamine (Calbiochem; San Diego, Calif.; 1 uM) (Sinha S & Chen J, "Purmorphamine activates the Hedgehog pathway by targeting Smoothened," Nature Chem. Biol. 2:29-30 (2006); Wu X, et al., "A small molecule with osteogenesis-inducing activity in multipotent mesenchymal progenitor cells," J. Am. Chem. Soc. 124:14520-14521 (2002)) for 2 weeks. Neuroepithelia grew rapidly and formed neural tube-like rosettes at day 14-17 of differentiation. The neuroepithelial colonies were gently blown off the surface by a pipette and grown as floating clusters in suspension in the same medium.

Olig2-expressing progenitors usually appeared around day 24 (Li et al., supra). The culture was then switched to a glial differentiation medium (modified Bottenstein-Sato medium; see, Bottenstein J, et al., "The growth of cells in serum-free hormone-supplemented media," Methods Enzymol. 58:94-109 (1979); and Bottenstein J, et al., "Selective survival of neurons from chick embryo sensory ganglionic dissociates utilizing serum-free supplemented medium," Exp. Cell Res. 125:183-190 (1980)) consisting of DMEM, N1 supplement (Sigma; St. Louis, Mo.), T3 (Sigma); 60 ng/ml), biotin (Sigma; 100 ng/ml) and cAMP (Sigma; 1 uM). FGF2 (R&D; 10 ng/ml) and/or EGF (Sigma; 10 ng/ml) was added to examine their effect on motor neuron differentiation and progenitor proliferation.

From the 5th week of differentiation, FGF2 was replaced with a cocktail of cytokines consisting of PDGFAA, IGF1 and NT3 (all at 10 ng/ml). Du Z, et al., "Induced expression of Olig2 is sufficient for oligodendrocyte specification but not for motoneuron specification and astrocyte repression," Mol. Cellular Neurosci. 33:371-380 (2006). SHH or purmorphamine was removed around 10 weeks when PDGFRα+ OPCs appeared. The cultures were fed every other day and the progenitor clusters were broken into smaller pieces with polished glass Pasteur pipette every week.

To differentiate OPCs to oligodendrocytes (MBP+, CNP+ and PLP/DM20+), progenitor clusters were incubated in Accutase® (Innovative Cell Technologies, Inc.; San Diego, Calif.) at 37° C. for 5 minutes. After removal of Accutase®, the loosened clusters were triturated and plated onto glass coverslips coated with poly-ornithine and a basement membrane material such as laminin in the glial differentiation medium without SHH/purmorphamine and heparin. The concentration of PDGF-AA, IGF1 and NT was 5 ng/ml.

To assess transplantability of these cells, progenitors enriched with OPCs after 10-12 weeks of hESC differentiation were dissociated with Accutase® and prepared in an artificial cerebral spinal fluid at 50,000 cells/ul. Caldwell M, et al., "Growth factors regulate the survival and fate of cells derived from human neurospheres," Nat. Biotechnol. 19:475-479 (2001). About 2 ul of a cell suspension (100,000 cells in total) was transplanted to the lateral ventricle of a newborn shiverer mouse with a glass pipette pulled for electrophysiology, as described previously. Guillaume D, et al., "Human embryonic stem cell-derived neural precursors develop into neurons and integrate into the host brain, "J. Neurosci. Res. 84:1165-1176 (2006); and Yandava B, et al., "'Global' cell replacement is feasible via neural stem cell transplantation: evidence from the dysmyelinated shiverer mouse brain," Proc. Nat. Acad. Sci. USA 96:7029-7034 (1999). The transplantation site was on the right side at 1 mm away from middle line between the Bregman and Lambda. Cells were injected 1 mm deep to target the ventricle and future corpus callosum.

Grafted (i.e., transplanted) animals were anesthetized and perfused with 4% paraformaldehyde at 3 months after transplantation. Brain tissues were dissected, post-fixed for 4 hours, and cryoprotected in 30% sucrose for histological analyses. For light microscopic analysis, brain tissues were cut into 25-um thick sections and sequentially collected in a 96-well plate in PBS containing 30% sucrose and glycine for free-floating immunostaining.

For electron microscopic analysis, brain tissues containing the corpus callosum from both transplanted and non-grafted mutant shiverer mice were dissected into chunks of about 1 $mm^3$. The tissue blocks were then processed and embedded in Epon™ (Hexion Specialty Chemicals; Houston, Tex.). Semi-thin (1 um) sections were stained with toluidine blue to identify myelin sheaths and thin sections were examined with a Hitachi Electronic Microscope (H-7000). Zhang S, et al., "Generation of oligodendroglial progenitors from neural stem cells," J. Neurocytol. 27:475-489 (1998).

Immuno-fluorescent staining on coverslip cultures and free-floating brain sections was described previously. Zhang et al. (2001), supra; Pankratz et al., supra. The following primary antibodies were used in the present study: anti-Olig2 (goat IgG, 1:500, sc-19969, Santa Cruz Biotechnology; Santa Cruz, Calif.), anti-βIII-tubulin (TuJ1, mIgG 1:5000, Sigma), anti-GFAP (mIgG 1:5000, Chemicon), anti-NG2 (mIgG 1:400, BD Pharmingen), anti-HB9 (mIgG 1:50, DSHB, Iowa City, Iowa), anti-PDGFRα (rat IgG 1:1000, gift from Dr. Stallcup WILLIAM STALLCUP, Burnham Institute for Medical Research, http://www.burnham.org/default.asp-?contentID=203) (Nishiyama A, et al., "Colocalization of NG2 proteoglycan and PDGF alpha-receptor on O2A progenitor cells in the developing rat brain," J. Neurosci. Res. 43:299-314 (1996)), anti-O4 (1:50, mouse IgM, Chemincon MAB345), MBP (1:500, rabbit IgG, Chemicon), anti-human nuclei (1:200, mouse IgG, Chemicon). Specificity of the antibodies was first tested in embryonic brain and spinal cord tissues. Li et al., supra; and Pankratz et al., supra. Negative controls without primary and secondary antibody were performed in all experiments to monitor non-specific staining The stained samples were visualized with a Nikon TE600 fluorescent scope equipped with a SPOT camera and software (Diagnostic Instruments; Sterling Heights, Mich.), as well as a Nikon Cl laser scanning confocal microscope.

For quantification of stained cell populations, optical fields were randomly selected with fixed ROI (region of interest) frame using cell counter plugin of ImageJ (Abramoff M, et al., "Image Processing with ImageJ," Biophoton. Int. 11:36-42 (2004)) from independent coverslips of the same group. At least three coverslips were counted for every group. The experiments were repeated three times with different batches of cells. Statistical analyses were performed using ANOVA with R (R_Development_Core_Team, 2007).

Results

Olig2 was Essential for OPC Differentiation.

Olig2 began to express in a subset of neural epithelial cells in the nuclei one week following SHH treatment (i.e., around day 23 of differentiation. The expression peaked at the 4-5th week of differentiation, and was largely maintained up to 6th week of differentiation. In the absence of SHH, very few Olig2-expressing cells were observed. The presence of cyclopamine, however, result in a near absence of Olig2 cells (see FIG. 1B, left column).

Replacement of SHH with purmorphamine (1 uM) resulted in earlier and more potent induction of Olig2 ($p<0.0001$) (see FIG. 1C). Purmorphamine at a concentration of 1 uM produced the highest proportion of Olig2 progenitors. In addition, purmorphamine resulted in an earlier (about 4-5 days) induction of Olig2 expression than SHH. Typically, purmorphamine-treated cultures generated a similar population of PDGFRα+ OPCs at around 13-14 weeks (see FIGS. 1B, 1E). Purmorphamine replaced SHH in Olig2 induction and OPC differentiation, which confirms the necessity of SHH signaling for OPC specification.

SHH Signaling was Required for Inducing Gliogenic Olig2 Progenitors.

Figure 2:
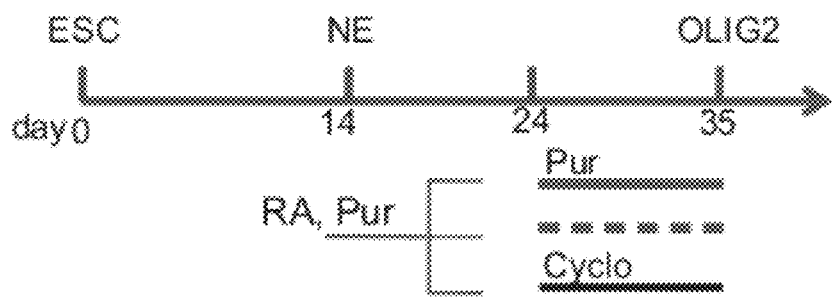
FIGS. 2A and 2B: SHH-dependent induction of NKX2.2 in the OLIG2 progenitors. (A) Experimental design showing three groups treated with purmorphamine (Pur), without purmorphamine, or with cyclopamine (cyclo) from day 24 to 35. (B) OLIG2 and NKX2.2 are expressed at day 24, but not in the same cell. At day 35, OLIG2 and NKX2.2 co-express only in cultures with SHH or purmorphamine. Bar=50 μm.
Figure 2:
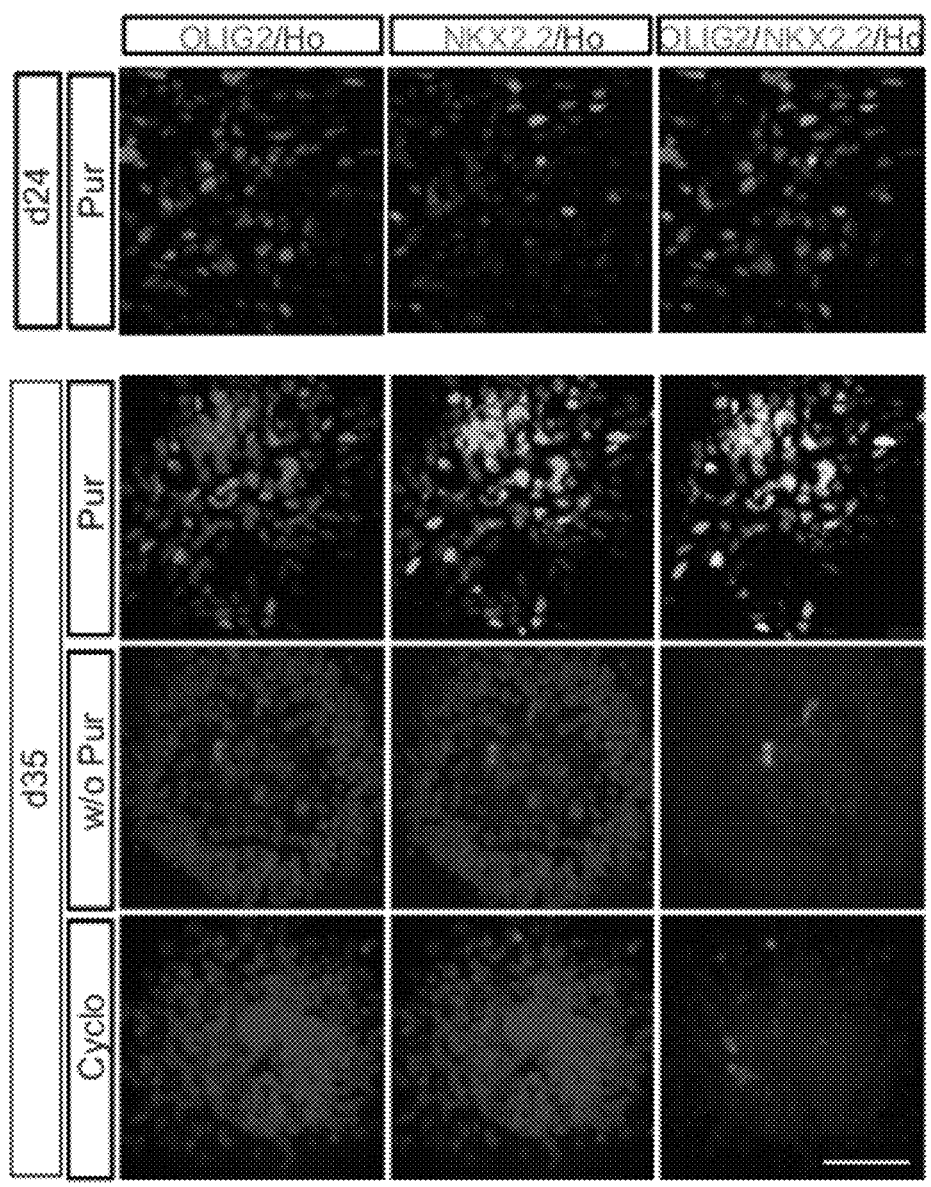

Immunostaining for Olig2 and Nkx2.2 indicated that some Nkx2.2-expressing cells were present by day 23 (before motor neuron differentiation), especially in the presence purmorphamine. Initially, Olig2 and Nkx2.2 did not overlap in the same cells (see FIG. 2B, upper panel). However, by the end of 5th week (following motor neuron generation), about half of the Olig2 cells co-expressed Nkx2.2 (see FIG. 2B, lower panel). Co-expression of Olig2 and Nkx2.2 is an indicator of OPCs in other vertebrates (Fu et al., supra; Qi et al., supra; and Zhou et al. (2001), supra. Thus, by the end of the 5th week, Olig2 progenitors were likely gliogenic. However, these Olig2 progenitors were negative for PDGFRα, NG2 or Sox10, markers of OPCs.

In the presence of SHH or purmorphamine from day 24 to 35, there was a sustained Olig2 progenitor population even after the phase of motor neuron differentiation. In contrast, removal of purmorphamine after the appearance of Olig2 progenitors (from day 24), or addition of cyclopamine, resulted in the near complete lack of cells expressing Olig2 and/or Nkx2.2, similar to the cultures in the absence of SHH/purmorphamine from the beginning (see FIG. 2B). Thus, not only the maintenance of Olig2 expression, but also the induction of Nkx2.2 in the Olig2 progenitors depends on SHH signaling.

Figure 3:
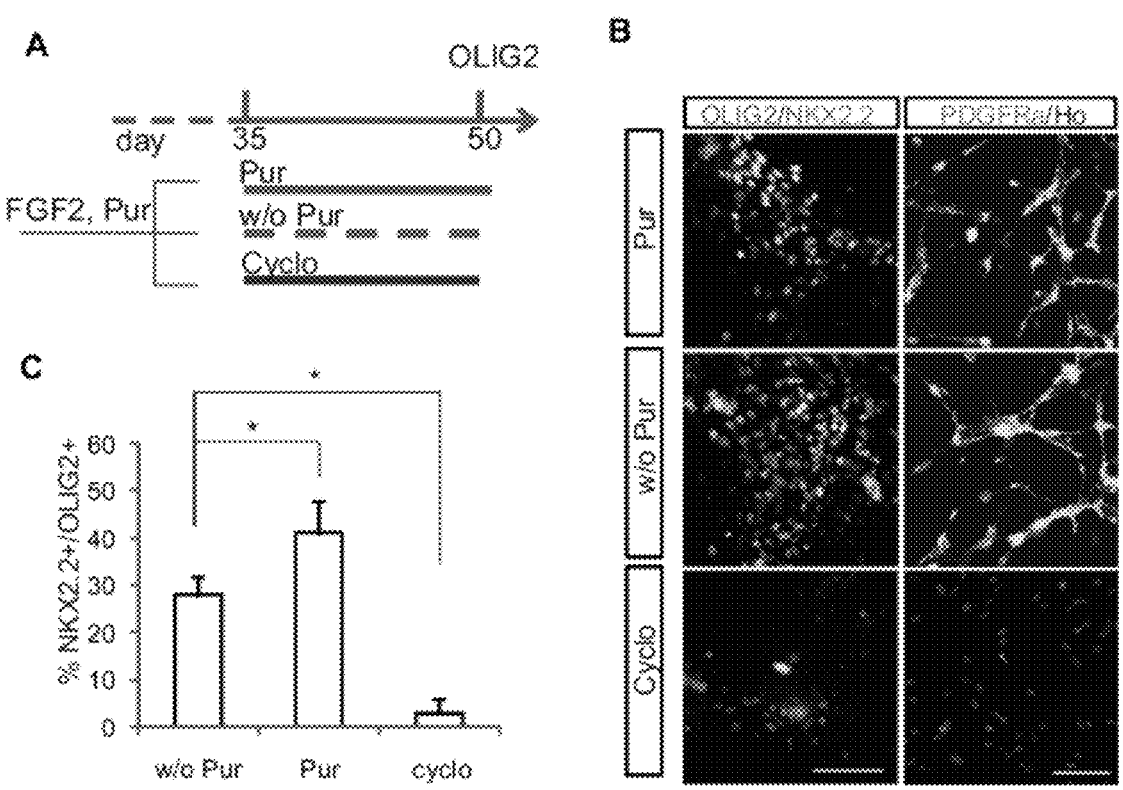
FIGS. 3A-3C: Requirement of SHH signaling for maintenance of OLIG2. (A) Experimental design showing OLIG2 enriched cells are treated with purmorphamine or cyclopamine until day 50. (B) At day 50, OLIG2$^+$/NKX2.2$^+$ population is present in cultures with or without purmorphamine but not in cultures with cyclopamine. PDGFRα$^+$ OPCs appear in both cultures with or without purmorphamine, but not in cultures with cyclopamine at day 100. (C) Quantitative analyses show proportion of OLIG2$^+$/NKX2.2$^+$ cells (*P=0.023 between groups with and without purmorphamine; P=0.0015 between groups without purmorphamine and with cyclopamine). Bar=50 μm.

Continued SHH signaling was required for maintaining gliogenic Olig2 progenitors. Gliogenic Olig2 progenitor cultures (day 35) were grown in the presence or absence of purmorphamine (1 uM), or the presence of cyclopamine (5 µM) for 2 weeks. Examination at day 50 indicated that Olig2, Nkx2.2 and Olig2/Nkx2.2 cells were present in the cultures with or without continued presence of purmorphamine, although about 40% more Olig2/Nkx2.2 double positive cells were seen in the purmorphamine-treated cultures over those with cyclopamine. However, the cultures treated with cyclopamine showed few cells expressing Olig2 and/or Nkx2.2, even though the cultures grew similarly as the other groups (see FIGS. 3B, C). RT-PCR analyses indicated that SHH was transcribed in cultured cells and there was a similar pattern of gene expression between cultures with and without purmorphamine. Thus, SHH signaling was continuously needed to maintain the Olig2 progenitors, even though exogenous SHH is now not necessary.

FGF2 Increased the Gliogenic Olig2 Progenitor Population by Inhibiting Motor Neuron Differentiation when Applied at the Induction of Olig2

Figure 4:
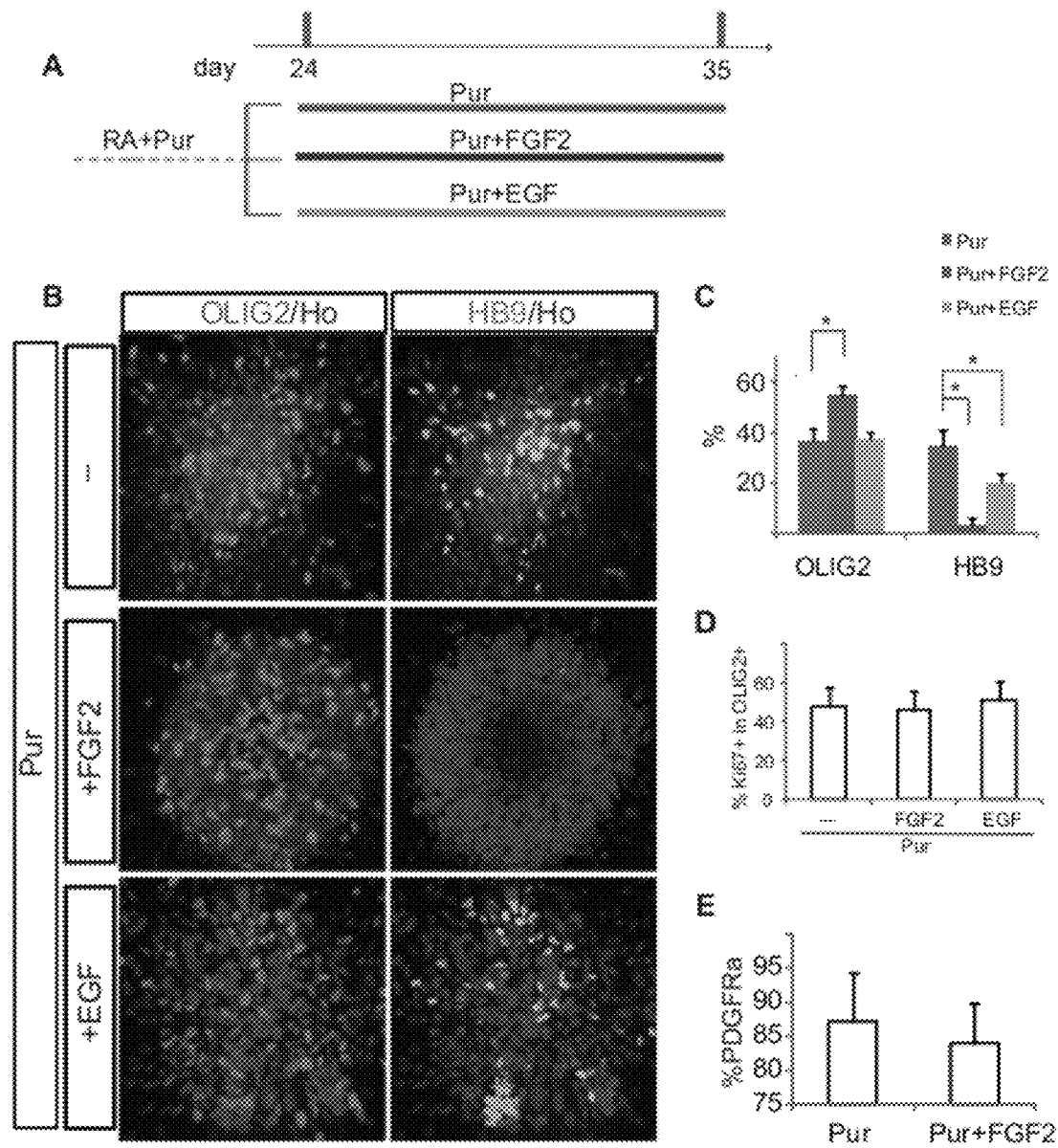
FIGS. 4A-4E: FGF2 inhibits motor neuron differentiation and increases OLIG2 progenitors. (A) Experimental design showing that the OLIG2$^+$ cells at day 24 are further cultured for 12 days in the presence of Pur alone, or combination of Pur with FGF2 or EGF. (B) When combined with Pur, FGF2, but not EGF, blocks HB9 expression (column II). (C) With presence of Pur, FGF2 but not EGF increases the OLIG2$^+$ cells by about 50% and decreases the HB9$^+$ cells to less than 5% whereas EGF moderately decreases HB9$^+$ cells. (D) FGF2, as well as EGF, does not selectively alter the Ki67$^+$ proportion in OLIG2$^+$ cells. (E) The proportion of PDGFRα$^+$ OPCs among total cells is similar between the FGF2-treated (for 12 days) and the control (without FGF2) cultures. Bar=50 μm. * indicates P<0.05 between the paired group.

FGF2 (10 ng/ml) was applied to the culture alongside purmorphamine at day 24 (following the appearance of Olig2, but before the differentiation of HB9+ motor neurons). Examination at day 35 showed that in the absence of FGF2, about 40-50% of the cells expressed HB9, a motor neuron-specific transcription factor, similar to previous observations. Li et al., supra; and Li X & Zhang S, "In vitro differentiation of neural precursors from human embryonic stem cells," Methods Mol. Biol. 331:169-177 (2006). In contrast, treatment with FGF2 nearly completely blocked HB9 expression. Accordingly, a much larger population (55%) of Olig2 cells was present when FGF2 was present early on. RT-PCR analyses confirmed that Ngn2 and HB9 expression was repressed. Cultures with FGF2 alone (without the presence of SHH or purmorphamine) had few, if any, HB9+ motor neurons or Olig2-expressing progenitors (see FIGS. 4B, C). Thus, FGF2 inhibited the transformation of Olig2 progenitors to HB9-expressing motor neurons, which was induced by RA and SHH, although FGF2 itself did not maintain Olig2 progenitors.

In another experiment, at day 35, FGF2 was removed, and RA was added back to the culture to create conditions for efficient motor neuron differentiation. Li et al., supra. Analyses of the cultures one to two weeks later indicated that there were hardly any HB9-expressing cells. Thus, FGF-treated Olig2 cells no longer generated motor neurons past the 5th week, corroborating an earlier finding that Olig2 progenitors become gliogenic at day 35.

To determine pro-proliferation effects of FGF2, we used another mitogen, EGF, as a control. Addition of EGF (10 ng/ml) for the same period did not increase the proportion of either Olig2 or Ki67 positive cells (see FIGS. 4B, C). Thus, FGF2 appeared to increase the Olig2+ cells by preventing the differentiation of Olig2 progenitors to motor neurons.

To determine if FGF2-treated Olig2 progenitor cultures generate OPCs, cultures treated with purmorphamine, purmorphamine plus FGF2, or cyclopamine between days 24 and 35 were differentiated to OPCs in the glial differentiation medium. Weekly analyses showed that few OPCs were present in the cyclopamine-treated cultures, whereas over 80% of cells were PDGFRα+ OPCs for both the purmorphamine and purmorphamine/FGF2 groups at 13-14 weeks of differentiation (see FIG. 4D). FGF2-treated cultures, however, generated substantially more total cells, hence more total OPCs as compared to the cultures with purmorphamine alone.

Continued Exposure to FGF2 Prohibited Transformation of Gliogenic Olig2 Progenitors to OPCs Purmorphamine/FGF2 treated-gliogenic Olig2 progenitors at day-35 were cultured in the presence or absence of FGF2. In the absence of FGF2, progenitor cultures did not expand. Immunostaining at the 7th week (2 weeks later) indicated that a similar population of Olig2/Nkx2.2 cells was present as at the 5th week. Conversely, and in the presence of FGF2, the Olig2 cells, especially the Olig2/Nkx2.2 population decreased, whereas Nkx2.2 progenitors did not appear to change significantly (see FIG. 5B). RT-PCR analyses indicated that FGF2 at this stage of culture compromises the effect of purmorphamine to maintain expression of Olig2, but promoted the expression of NFIA.

Figure 5A:
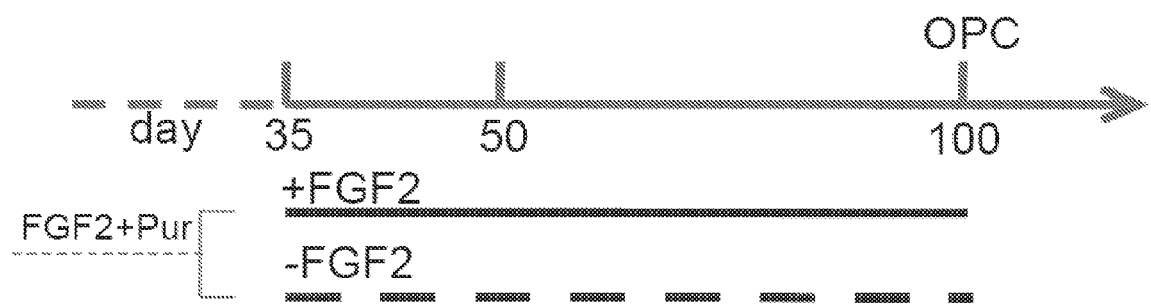
FIGS. 5A-5H: FGF2 inhibits the transformation of OLIG2 progenitors to OPCs by inhibiting co-expression of OLIG2 and NKX2.2. (A) Experimental design showing that the gliogenic OLIG2 progenitors at day 35 are treated with or without FGF2 and then examined at day 50 or day 100. (B) At day 50 (left column), the majority of the cells co-express OLIG2 and NKX2.2 whereas few double positive cells are present in cultures with FGF2 (left column). At day 100 (right columns), cultures without FGF2 (upper row) contain mostly PDGFRα cells with few cells positive for βIII-tubulin or GFAP. In the presence of FGF2, the majority cells are positive for βIII-tubulin or GFAP (lower row). Scale bar=100 μm (C) A higher population of cells expressing OPC markers (% PDGFRα, SOX10, NG2 cells among total cells) is generated in the absence of FGF2 at day 100. (D) Population of PDGFRα$^+$, βIII-tubulin+ and GFAP+ cells in the presence or absence of FGF2 at day 100. (E) FGF2 treatment results in a lower proportion of OLIG2/NKX2.2 double positive cells at day 50. *P=0.048; **P=0.0018, n=3. (F) FACS analysis at day 50 shows a slight decrease (10%) in the OLIG2+ population and a left shift (indicating decreased expression level in individual cells) for the group with FGF2 than without FGF2. (G-H) Quantitative RT-PCR at day 50 showing FGF2 decreases SHH by half and increases the transcription of GLI2 and GLI3.
Figure 5B:
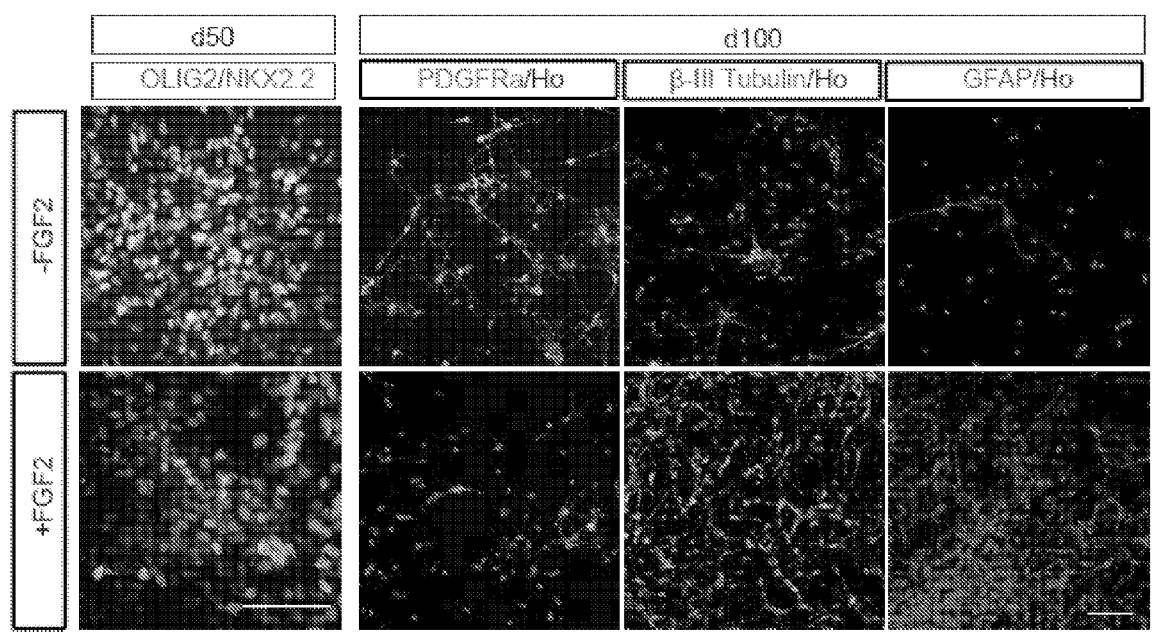
Figure 5C:
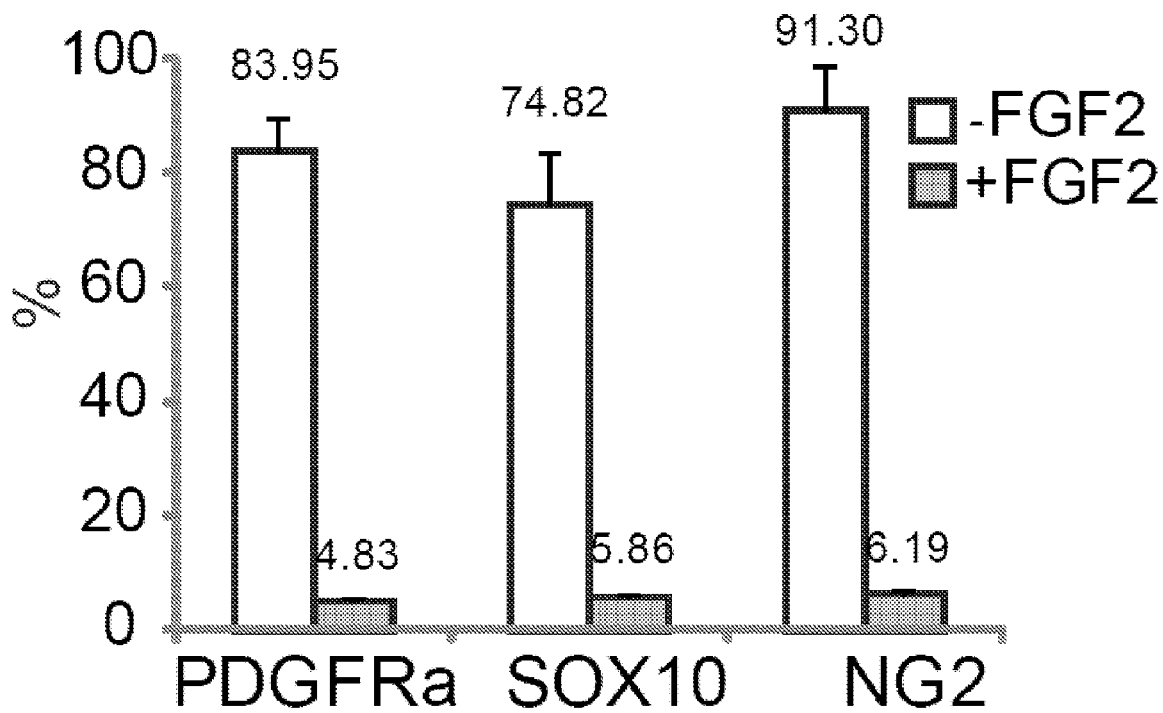
Figure 5D:
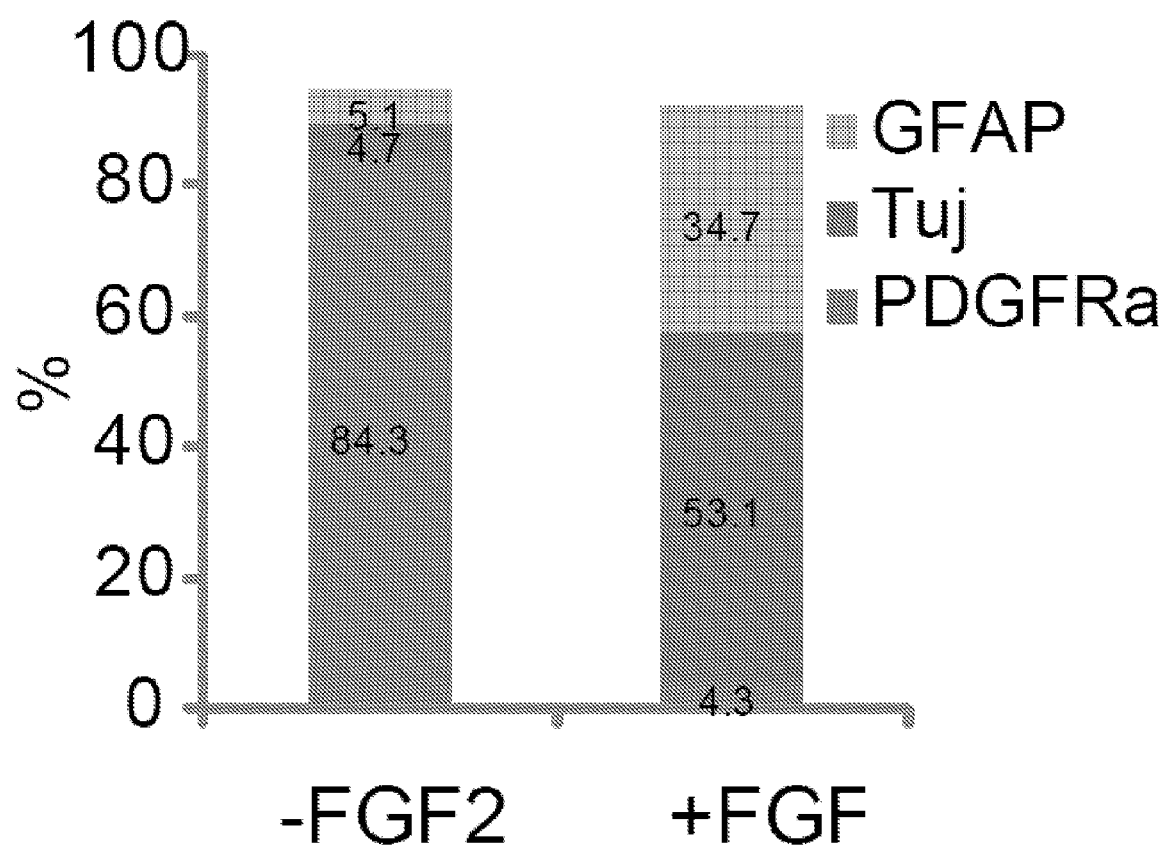
Figure 5E:
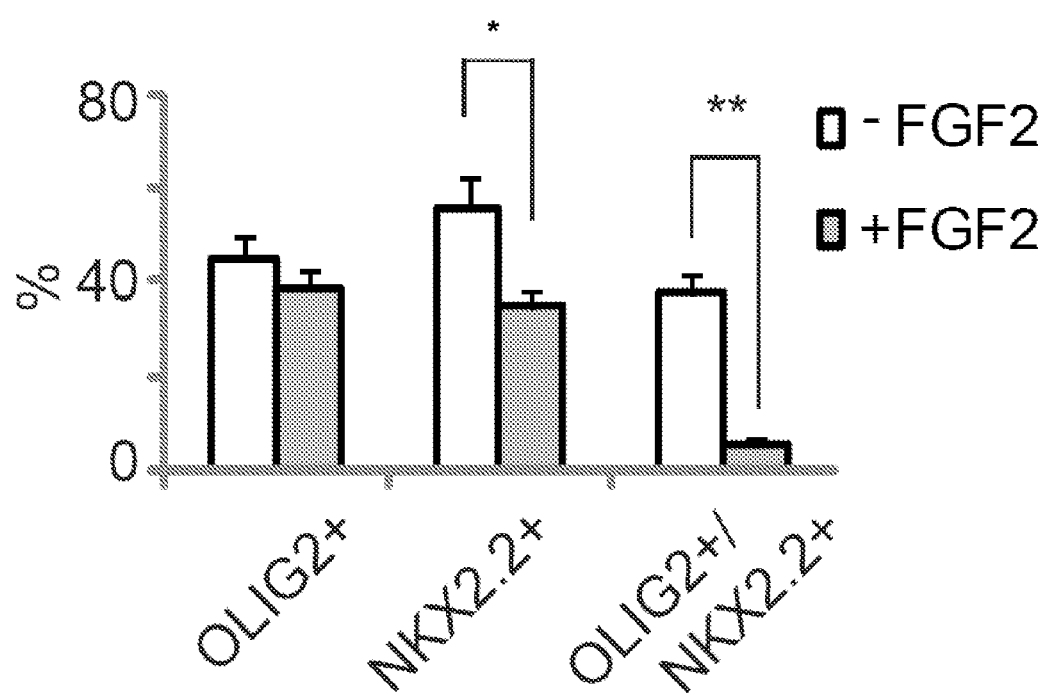
Figure 5F:
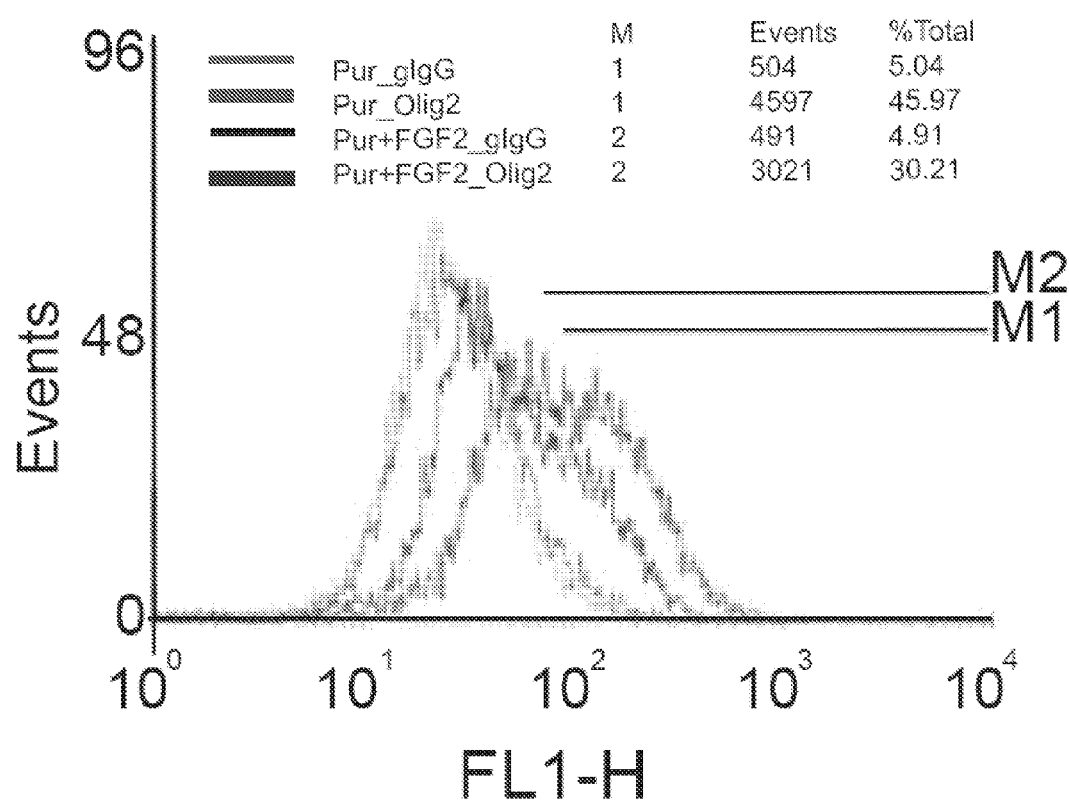
Figure 5G:
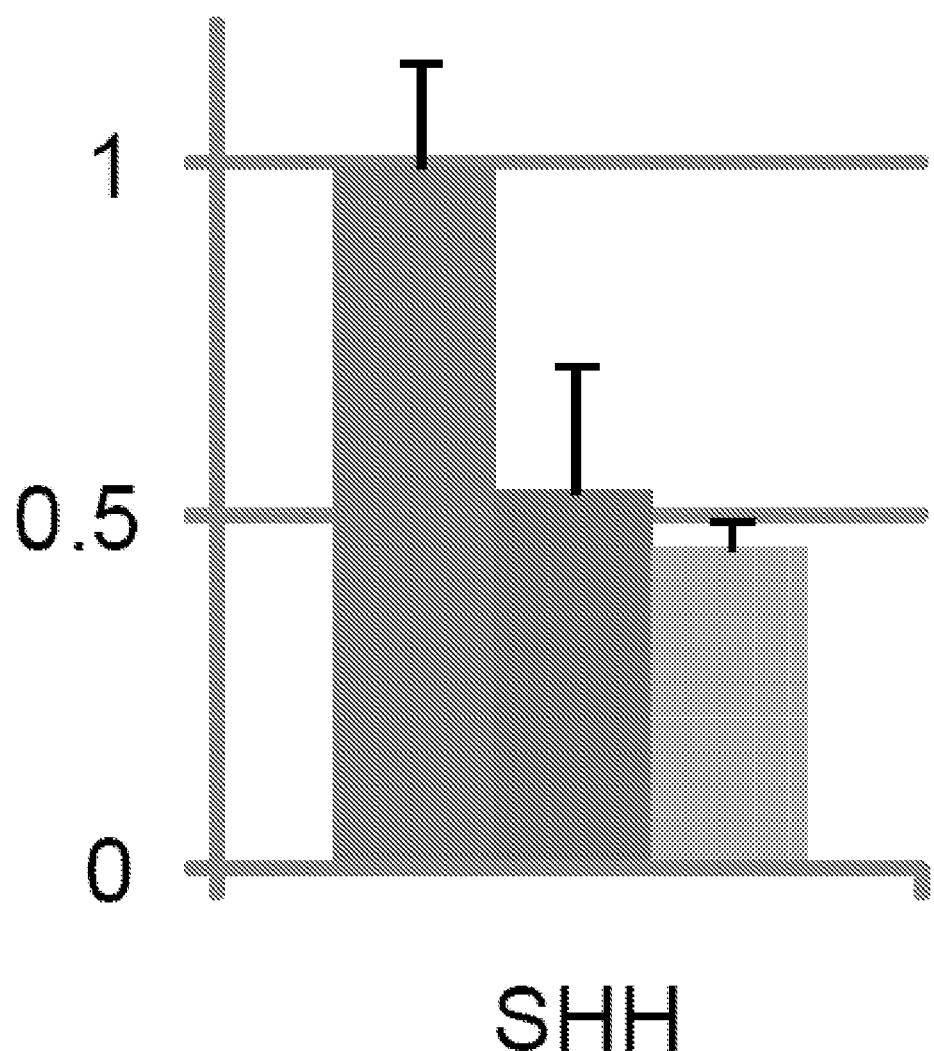
Figure 5H:
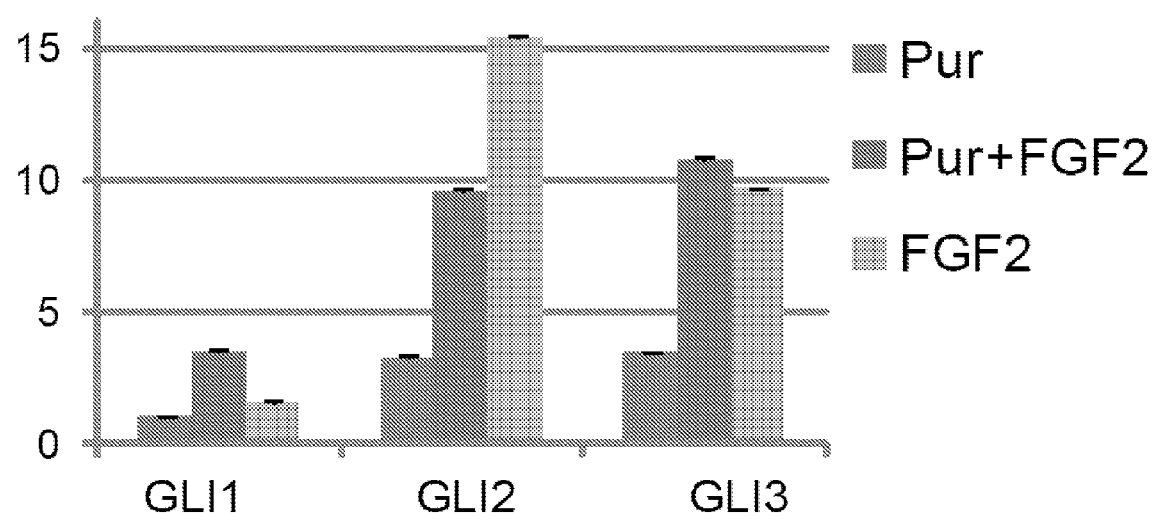

Weekly differentiation of the progenitors (after removal of FGF2 and purmorphamine) indicated that by 13-14 weeks in the absence of FGF2, the majority of the cells (84%) adherent to the culture surface exhibited a typical bipolar or tripolar OPC morphology (See FIGS. 5B, C, D). These cells were positively stained for multiple OPC markers, such as NG2, PDGFRα, Sox10, Olig2 and Nkx2.2 (see FIG. 5C). Very few cells stained positively for a neuronal marker, βIII-tubulin, or an astrocytic antigen, GFAP (see FIGS. 5B, D). Conversely, weekly differentiation of progenitors cultured in the presence of FGF2 throughout resulted in cultures that possessed few PDGFRα+ OPCs (4%), whereas the majority of cell populations were βIII tubulin+ neurons (53%) and GFAP+ astrocytes (35%). Thus, FGF2 inhibited OPCs, but favored neuronal and astrocytic differentiation from the Olig2/Nkx2.2 progenitors.

The Transition from the Gliogenic Olig2 Progenitors to OPCs was Prolonged Compared to the Transition Observed in other Vertebrates.

Olig2/Nkx2.2 progenitors appeared mostly at around 5th week, right after the phase of motor neuron differentiation. However, PDGFRα and Sox10 positive OPCs did not appear until 5-8 weeks later (or 10-13 weeks total) in the same glial differentiation medium as previously used for mouse cells. Addition of SHH (purmorphamine), FGF2, EGF or combination of FGF2 (EGF) and SHH did not speed up the differentiation of OPCs marked by PDGFRα, NG2 and Sox10. Addition of Noggin (100 ng/ml) at day 35, a BMP antagonist known to promote OPC differentiation (Mehler M, et al., "Developmental changes in progenitor cell responsiveness to bone morphogenetic proteins differentially modulate progressive CNS lineage fate," Dev. Neurosci. 22:74-85 (2000)) and used by some for oligodendrocyte differentiation from hESCs (Izrael et al., supra), together with SHH (100 ng/ml), did not result in earlier differentiation of OPCs. Together, these findings suggested an intrinsic program governing the transition from the gliogenic Olig2 cells to OPCs.

hESC-Derived OPCs Differentiated to Oligodendrocytes In Vitro

Analyses on signaling requirement during multiple stages, as described above, resulted in the present 3-month-long differentiation of OPCs from hESCs (see FIG. 6A). After 13-14 weeks of hESC differentiation, the plated OPCs initially exhibited a bipolar morphology (see FIGS. 6B, C). The vast majority were co-expressing Olig2 and Nkx2.2 in the cell nuclei (See FIG. 6D). They now stained positively for Sox10 in the cell nuclei (See FIG. 6E). In addition to the oligodendroglial transcription factors, these cells co-expressed PDGFRα and NG2 on the membrane and processes (See FIGS. 6F, G).

Over the course of subsequent 2-4 weeks, these bipolar cells became multipolar (see FIG. 6H) and were positive for an immature oligodendrocyte marker O4 (see FIG. 6I). The O4+ cells were no longer positive for PDGFRα, similar to our previous finding using fetal brain tissue derived progenitor cultures. Zhang et al. (2000), supra. Another commonly used OPC marker NG2, however, often overlapped with O4.

With further culturing for 6-8 weeks, enriched oligodendroglia tend to die under the serum-free condition. Nevertheless, surviving cells exhibited more elaborated processes, occasionally with membrane sheaths. These cells were stained positively for MBP (see FIG. 6J), which is normally expressed by mature oligodendrocytes.

hESC-generated OPCs produced myelin sheaths in vivo. The myelination potential of the in vitro produced OPCs was investigated by transplanting the OPCs (differentiated from hESCs for 12 weeks) into the ventricle of neonatal shiverer mice. The shiverer mice do not produce compact myelin sheaths due to a complete lack of myelin basic protein. Histological analyses at three months following transplantation indicated that grafted human cells, as identified by specific human nuclear protein staining, were present, preferentially, in the corpus callosum (See FIG. 6K). Virtually every human nuclear protein positive cell also positively stained for Olig2 (See FIG. 6L).

Most of the human cells displayed numerous processes and positively stained for MBP (See FIGS. 6K, M). These MBP-expressing processes connected to the neurofilament positive axons in the corpus callosum (See FIG. 6N). No human cells were co-labeled for GFAP, typically expressed by astrocytes in the central nervous system (See FIG. 6O). Toluidine blue staining on the Epon-embedded semi-thin sections showed extensive myelin sheaths in grafted animals, but not in non-transplanted shiverer mice (See FIG. 6P). Electron microscopic analyses confirmed that there were compact myelin sheaths in the corpus callosum of the transplanted mice (See FIGS. 6Q, R), whereas no compact myelin sheaths were present in the non-transplanted shiverer mice.

TABLE 2

Oligodendrocyte Precursor Cells - Preferred Culture Conditions and Markers
Method of Generating Oligodenrocytes from hESCs

| | Time-frame | | | | | | | | |
|---|---|---|---|---|---|---|---|---|---|
| | Days 1-4 | Days 5-7 | Days 7-14 | Days 14-24/25 | Week 3.5-5 | Week 5 | Week 10 | Week 10-12 | Week 12 |
| Culture Conditions | Suspension of hESCs | hESC aggregates | Neural tube-like rosette formation | Olig2 induction | Gliogenic Olig2+ progenitors | Remove FGF2 | PDGFR+/Olig2+ OPCs | OPC culture | Oligodendrocyte differentiation |
| Medium Additives | ESC medium | NSM | Laminin substrate; 0.1 μM | NSM; 0.1 μM RA (day 10); 100 ng/ml SHH | Glia medium; SHH or purmorphamine; | Glia medium; SHH or purmorphamine; | Glia medium; CSS; Remove SHH or | Glia medium; CSS | poly-ornithine and laminin substrate; Glia |

TABLE 2-continued

Oligodendrocyte Precursor Cells - Preferred Culture Conditions and Markers
Method of Generating Oligodenrocytes from hESCs

| Time-frame | | | | | | | | |
|---|---|---|---|---|---|---|---|---|
| Days 1-4 | Days 5-7 | Days 7-14 | Days 14-24/25 | Week 3.5-5 | Week 5 | Week 10 | Week 10-12 | Week 12 |
| | | RA | (day 15) or 1 µM purmorphamine (day 15) | optionally 10 ng/ml FGF2 | CSS | purmorphamine at week 8 | | medium; ½ CSS for one week, removed for further differentiation |

ESC medium: DMEM/F12; 1x non-essential amino acids (NEAA); 20% knockout serum replacement (KSR); 292 mg/ml glutamine and 0.1 mM 2-mercaptoethanol.
Neural sphere medium (NSM): DMEM/F12; N2 supplement and NEAA.
Glia medium: modified from Bottenstein-Sato medium (DMEM with insulin); B27; N1 supplement, 60 ng/ml T3, 100 ng/ml biotin, 1 µM cAMP; see Bottenstein J, et al., "The growth of cells in serum-free hormone-supplemented media," Methods Enzymol. 58: 94-109 (1979).
Cocktail Survival supplements (CSS): PDGF; IGF and NT3 (all at 10 ng/ml).

What is claimed is:

1. A method of generating a population of oligodendroglial precursor cells, the method comprising the steps of:
   (a) differentiating isolated pluripotent stem cells into a population of early rosette cells that are Pax6+/Sox1-;
   (b) culturing early rosette cells in the presence of retinoic acid and an agent that activates a sonic hedgehog pathway to obtain a population of cells having a neural tube-like rosette morphology that are Pax6+/Sox1+;
   (c) culturing the neural tube-like rosette cells in the presence of an agent that activates a sonic hedgehog pathway and FGF-2 to obtain Olig2-expressing progenitor cells; and
   (d) culturing the Olig2-expressing progenitors cells in the presence of the agent that activates the sonic hedgehog pathway, but in the absence of retinoic acid and in the absence of FGF-2, to obtain PDGFRα+/SOX10+/OLIG2+/NKX2.2+ oligodendroglial precursor cells.

2. A method as recited in claim 1, wherein the agent that activates the sonic hedgehog is added within one week after the addition of retinoic acid.

3. A method as recited in claim 1, wherein the agent that activates the sonic hedgehog pathway is selected from sonic hedgehog and purmorphamine.

4. A method as recited in claim 3, wherein sonic hedgehog is between 50 to 500 ng/ml (±10%).

5. A method as recited in claim 3, wherein purmorphamine is between 0.5 to 1.2 µM (±10%).

6. A method as recited in claim 1, wherein the retinoic acid is between 0.05 to 0.3 µM (±10%).

7. A method as recited in claim 1, wherein the FGF-2 is between 2 to 30 ng/ml (±10%).

8. A method as recited in claim 1, wherein the FGF-2 is not present after day 35.

9. A method as recited in claim 1, wherein the pluripotent stem cells are primate embryonic stem cells.

10. A method as recited in claim 1, wherein the pluripotent stem cells are human embryonic stem cells.

11. A method as recited in claim 1, wherein the pluripotent stem cells are primate induced pluripotent cells (iPS cells).

12. A method as recited in claim 1, wherein the pluripotent stem cells are human induced pluripotent cells (iPS cells).

13. A method of generating a population of oligodendroglial cells, the method comprising the steps of:
   (a) obtaining cells having a neural tube-like rosette morphology that are Pax6+/Sox1+;
   (b) culturing the neural tube-like rosette cells in the presence of retinoic acid and an agent that activates a sonic hedgehog pathway to obtain Olig2-expressing progenitor cells;
   (c) culturing the progenitor cells in the presence of an agent that activates a sonic hedgehog pathway to obtain Olig2/Nkx2.2-expressing glial progenitor cells;
   (d) culturing the Olig2/Nkx2.2-expressing glial progenitors in the presence of the agent that activates the sonic hedgehog pathway, but in the absence of retinoic acid, to obtain PDGFRα+ oligodendroglial precursor cells; and
   (e) culturing the PDGFRα+ oligodendroglial precursor cells on an extracellular matrix material in the absence of the agent that activates the sonic hedgehog pathway to obtain oligodendroglial cells.

14. A method as recited in claim 10, wherein the extracellular matrix material is selected from a basement membrane preparation, collagen, hyaluronic acid, gelatin, elastin, fibronectin, laminin and mixtures thereof.

15. A method of generating a population of oligodendroglial precursor cells, the method comprising the steps of:
   (a) obtaining early rosette cells (Pax6+/Sox1);
   (b) culturing the Pax6+/Sox1 early rosette cells in the presence of retinoic acid and an agent that activates a sonic hedgehog pathway to obtain a population of cells having a neural tube-like rosette morphology that are Pax6+/Sox1+;
   (c) culturing the neural tube-like rosette cells in the presence of an agent that activates a sonic hedgehog pathway and FGF-2 to obtain Olig2-expressing progenitor cells; and
   (d) culturing the Olig2-expressing progenitors cells in the presence of the agent that activates the sonic hedgehog pathway, but in the absence of retinoic acid and in the absence of FGF-2, to obtain PDGFRα+/SOX10+/OLIG2+/NKX2.2+ oligodendroglial precursor cells.

16. The method of claim 15 wherein the agent of step (b) is selected from sonic hedgehog and purmorphamine.

* * * * *